United States Patent [19]

Agouridas et al.

[11] Patent Number: 5,439,890
[45] Date of Patent: Aug. 8, 1995

[54] ERYTHROMYCIN DERIVATIVES

[75] Inventors: Constantin Agouridas; Jean-François Chantot, both of Nogent sur Marne; Nicole Tessot, Claye-Souilly, all of France

[73] Assignee: Roussel-Uclaf, France

[21] Appl. No.: 340,026

[22] Filed: Nov. 14, 1994

[30] Foreign Application Priority Data

Dec. 3, 1993 [FR] France ................. 93 14505

[51] Int. Cl.⁶ ............... A61K 31/70; C07H 17/08
[52] U.S. Cl. ................... 514/29; 536/7.2; 536/7.3; 536/7.4
[58] Field of Search ............. 536/7.3, 7.2, 7.4; 514/29

[56] References Cited

FOREIGN PATENT DOCUMENTS 0487411  5/1992  European Pat. Off. ............. 536/7.3

*Primary Examiner*—Douglas W. Robinson
*Assistant Examiner*—James O. Wilson
*Attorney, Agent, or Firm*—Bierman and Muserlian

[57] ABSTRACT

A compound of the formula

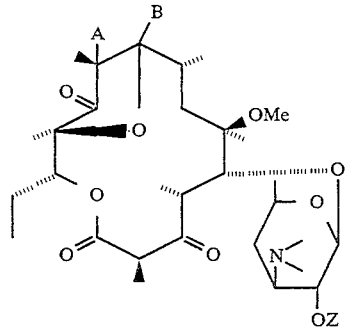

wherein A and B are both hydrogen or A is hydrogen and B is —OH or A and B form a carbon-carbon double bond and Z is hydrogen or acyl of an organic carboxylic acid of 1 to 6 carbon atoms and their nontoxic, pharmaceutically acceptable acid addition salts having antibiotic activity.

12 Claims, No Drawings

ERYTHROMYCIN DERIVATIVES

OBJECTS OF THE INVENTION

It is an object of the invention to provide the erythromycin derivatives of formula I and a process for their preparation.

It is another object of the invention to provide novel antibiotic compositions and a method of combatting bacterial infections in warm-blooded animals.

These and other objects and advantages of the invention will become obvious from the following detailed description.

THE INVENTION

The novel erythromycin compounds of the invention are a compound selected from the group consisting of a compound of the formula

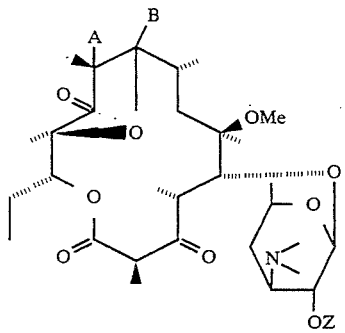

I wherein A and B are both hydrogen or A is hydrogen and B is —OH or A and B form a carbon-carbon double bond and Z is hydrogen or acyl of an organic carboxylic acid of 1 to 6 carbon atoms and their non-toxic, pharmaceutically acceptable acid addition salts.

Among the preferred compounds of formula I are those wherein Z is hydrogen and those wherein A and B form a carbon-carbon double bond. Particularly preferred is 3-de((2,6-dideoxy-3-C-methyl-3-O-methyl-α-L-ribohexopyranosyl)-oxy)-9-deoxo-9,10-didehydro-11,12-dideoxy-3,11-dioxo-9,12-epoxy-6-O-methyl-erythromycin.

Examples of suitable acids to form the acid addition salts are inorganic acids such as sulfuric acid, nitric acid, hydrochloric acid and hydrobromic acid and organic acids such as formic acid, acetic acid, citric acid, benzoic acid and methane sulfonic acid.

The process of the invention for the preparation of compounds of formula I comprises reacting a compound of the formula

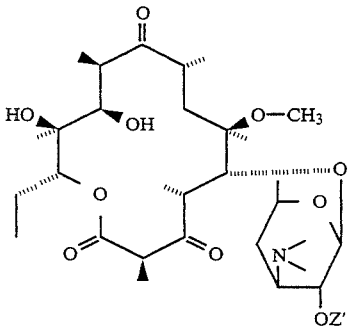

II wherein Z' is acyl of an organic carboxylic acid of 1 to 6 carbon atoms with an agent capable of introducing a 9 (12)-epoxy bridge and simultaneously oxidizing the 11-hydroxy group to form a compound of the formula

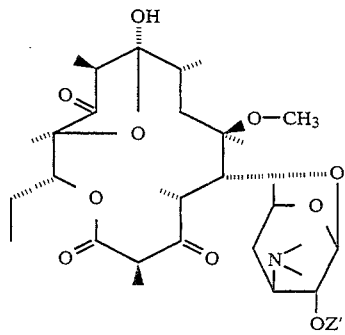

$I_A$ optionally subjecting the latter either to the action of a releasing agent of the 2'-hydroxyl to obtain a compound of the formula

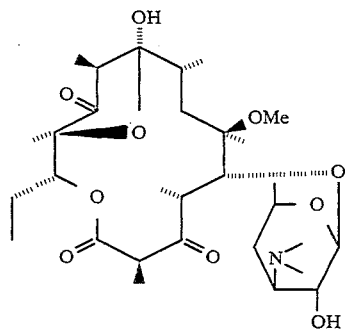

$I_B$ or to the action of a dehydration agent to obtain a compound of the formula

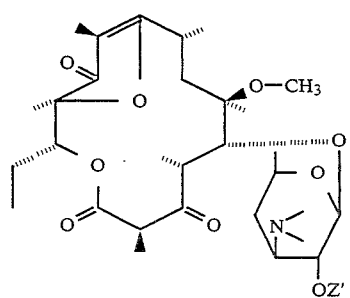

$I_C$ then optionally subjecting the latter compound to the action of a releasing agent of the 2'-hydroxyl to obtain a compound of the formula

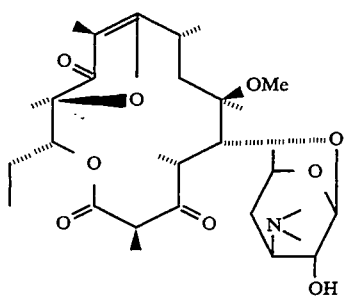

$I_D$ subjecting the compound of formula $I_C$ to the action of a reducing agent of the 9(10)-double bond to obtain a compound of the formula

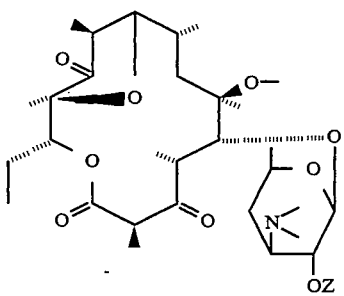

$I_E$ and optionally subjecting the latter to the action of a releasing agent of the 2'-hydroxyl to obtain a compound of the formula

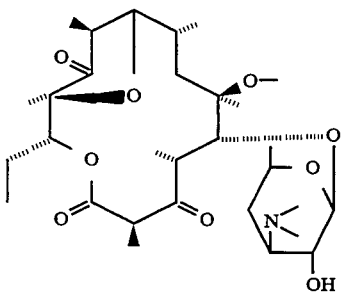

$I_F$

The compounds of formula II used as starting products of the process of the invention are described in the European Patent Application No. 487,411.

Preferably, the oxidation in the 11-position and the simultaneous obtaining of the 9(12) epoxide bridge is carried out with oxalyl chloride in dimethylsulfoxide in the presence of a base, preferably triethylamine and the release of the 2'-hydroxyl is carried out by methanolysis. The esterification may be carried out using an acid by standard processes, the dehydration in 9(10) position is carried out with hydrochloric acid, or any other acid of fluoro or perfluoroacetic acid or sulfuric acid type, and the reduction of the 9(10) double bond is carried out using diisobutylaluminium hydride (DIBAH), or by catalytic hydrogenation in the presence of an acid as defined above.

The novel antibiotic compositions of the invention are comprised of an antibiotically effective amount of a compound of formula I and an inert pharmaceutical carrier. The compositions may be in the form of tablets, dragees, capsules, granules, creams, gels, ointments, suppositories and injectable solutions or suspensions.

Examples of suitable excipients or carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The compositions have a good antibiotic activity on gram bacteria such as staphylococci, streptococci and pneumococci and are useful in the treatment of infections caused by sensitive germs, particularly of staphylo-coccia such as staphylococcal septicemia, malignant staphylococcia of the face or skin, pyodermititis, septic or suppurating sores, boils, anthrax, phlegmons, erysipelas and acne, staphylococcia such as primary or post-influenzal acute anginas, bronchopneumonia, pulmonary suppurations, streptococcal infection such as acute anginas, otitis, sinusitis, scarlet fever, pneumococcal infection such as pneumonia, bronchitis; brucellosis, diphtheria, gonococcal infection. The compositions are also active against infections caused by germs such as Haemophilus influenzae, Rickettsia, Mycoplasma pneumoniae, Chlamydia, Legionella, Ureaplasma, Toxoplasma.

The novel method of the invention for combatting bacterial infections in warm-blooded animals, including humans, comprises administering to warm-blooded animals an antibacterically effective amount of at least one compound of the formula I and their non-toxic, pharmaceutically acceptable acid addition salts. The compounds may be administered orally, rectally, parenterally or topically to the skin or mucous membranes. The usual daily dose is 0.6 to 4 mg/kg depending on the condition treated, the specific compound and the method of administration.

In the following examples, there are described several preferred embodiments to illustrate the invention. However, it is to be understood that the invention is not intended to be limited to the specific embodiments.

EXAMPLE 1

(9S) 3-de(2,6-dideoxy-3-C-methyl-3-O-methyl-α-L-ribohexopyranosyl) oxy)-9-deoxo-11,12-dideoxy-3,11-dioxo-9,12-epoxy-9-hydroxy-6-O-methyl-erythromycin STAGE A: (9S) 3-de-(2,6-dideoxy-3-C-methyl-3-O-methyl-α-L-ribohexopyranosyl)-oxy)-9-deoxo-11,12-dideoxy-3,11-dioxo-9,12-epoxy-9-hydroxy-6-O-methyl-erythromycin-2'-acetate 2.8 ml of oxalyl chloride in solution in 30 ml of methylene chloride were cooled to −70° C. and 4 ml of dimethylsulfoxide in solution in 3 ml of methylene chloride were added. The mixture was stirred for a few minutes at −70° C. and 2 g of 3-de[2,6-dideoxy-3-C-methyl-3-O-methyl-α-L-ribohexopyranosyl)-oxy]-6-O-methyl-3-oxo-erythromycin-2'-acetate [prepared as indicated in the European Patent No. 487,411, Example 3C 1], in solution in 10 ml of methylene chloride were introduced. The mixture was stirred for 65 minutes at −70° C. and 20 ml of triethylamine were added over 2 hours. The temperature was allowed to rise to ambient temperature and was stirred for one hour at this temperature. The reaction medium was diluted with methylene chloride and the organic phase was washed, dried, filtered and concentrated to dryness to obtain 2.06 g of product which was purified by chromatography and eluting with a methylene chloride—methanol—ammonium hydroxide mixture (98-2-0.2) to obtain 575 mg of the desired product.

| IR Spectrum, CHCl$_3$ | |
|---|---|
| absence 9 keto | |
| OH | 3578 cm$^{-1}$ |
| C=O | 1750–1712 cm$^{-1}$ |
| Bohlman bands —N= | |
| NMR CDCl$_3$ ppm | |
| H$_{10}$ | 2.55–2.75 ppm |

STAGE B: (9S) 3-de(2,6-dideoxy-3-C-methyl-3-O-methyl-α-L-ribohexopyranosyl)-oxy)-9-deoxo-11,12-dideoxy-3,11-dioxo-9,12-epoxy-9-hydroxy-6-O-methyl-erythromycin A solution of 100 mg of the product of Stage A and 1 ml of methanol was stirred for 3 days at ambient temperature and 100 mg of product were obtained which was purified by chromatography and eluting with an ethyl acetate-triethylamine mixture (95-5) to obtain 73 mg of the desired product.

NMR CDCl$_3$ 2.29 (s): N-(CH$_3$)$_2$; 4.37 (d): H'$_1$; 3.20 (dd): H'$_2$; 2.50 (dd): H'$_3$; 3.51 (dd): H'$_5$.

EXAMPLE 2

3-de((2,6-dideoxy-3-C-methyl-3-O-methyl-α-L-ribohexopyranosyl)-oxy)-9-deoxo-9,10-didehydro-11,12-dideoxy-3,11-dioxo-9,12-epoxy-6-O-methyl-erythromycin STAGE A: (9S) 3-de((2,6-dideoxy-3-C-methyl-3-O-methyl-α-L-ribohexopyranosyl)-oxy)-9-deoxo-9,10-didehydro-11,12-dideoxy-3,11-dioxo-9,12-epoxy-6-O-methyl-erythromycin-2'-acetate 8.5 ml of a 2N hydrochloric acid solution were added to a solution of 1.28 g of the product of Example 1 of Stage A and 20 ml of ethanol and the mixture was stirred for 16 hours and then concentrated to dryness. The pH was brought to 7-8 by the addition of an aqueous solution of sodium bicarbonate and extraction was carried out with methylene chloride. The extracts were dried, filtered and concentrated to dryness to obtain 1.1 g of the desired product which was purified by chromatography on silica and eluting with a methylene chloride—methanol—ammonium hydroxide mixture (98-2-0.2) to obtain 575 mg of the desired product.

| NMR CDCl$_3$ | |
|---|---|
| Absence of proton in position 10 | |
| H$_3$ and H$_8$ | 2.5 to 2.8 |
| H$_4$ | 2.58 |

STAGE B: 3-de((2,6-dideoxy-3-C-methyl-3-O-methyl-α-L-ribohexopyranosyl)-oxy)-9-deoxo-9,10-didehydro-11,12-dideoxy-3,11-dioxo-9,12-epoxy-α-O-methyl-erythromycin A mixture of 50 mg of the product of Stage A and 2 ml of methanol was stirred overnight at ambient temperature and after evaporation to dryness, 40 mg of the crude desired product were purified by chromatography on silica and eluting with an ethyl acetate-triethylamine mixture (95-5) to obtain 45.1 mg of the desired product.

| NMR CDCl$_3$ ppm | |
|---|---|
| H'$_1$ | 4.30 (d) |
| H'$_2$ | 3.18 (dd) |
| H'$_3$ | 2.45 (m) |
| H'$_5$ | 3.51 (m) |
| 227 (J) N (Me)$_2$ | |

| Analysis: | Calculated | Found |
|---|---|---|
| C = | 63.40% | 63.1% |
| H = | 8.7% | 8.8% |
| N = | 2.46% | 2.3% |

EXAMPLE 3

3-de((2,6-dideoxy-3-C-methyl-3-O-methyl-α-L-ribohexopyranosyl)-oxy)-9-deoxo-11,12-dideoxy-3,11-dioxo-9,12-epoxy-6-O-methyl-erythromycin The product was prepared by reducing the compound of Stage A of Example 2 and then releasing the hydroxyl in position 2' by methanolysis.

Examples of Pharmacological Compositions

Tablets were prepared containing 150 mg of the product of Example 2 and sufficient excipient of starch, talc and magnesium stearate for a tablet of 1 g.

PHARMACOLOGICAL STUDY

A) Activity in vitro.

Method of dilutions in a liquid medium.

A series of tubes were prepared into which an equal quantity of sterile nutritive medium was divided. Increasing quantities of the product under study were distributed into each tube and then each tube was seeded with a bacterial strain. After incubation for twenty-four hours in an oven at 37° C., the growth inhibition was evaluated by transillumination which allows the minimal inhibiting concentrations (M.I.C.), expressed in micrograms/ml, to be determined. The results obtained with the product of Example 2 are as follows: reading after 24 hours.

| | |
|---|---|
| *Streptococcus pyogenes* group A 02A1UC1 | 1.2 |
| *Streptococcus agalactiae* group B02B1HT1 | 0.15 |
| *Streptococcus faecalis* group D 02D2UC1 | 1.2 |
| *Streptococcus faecium* group D 02D3HT1 | 1.2 |
| Streptococcus group G 02G0GR5 | 0.6 |
| *Streptococcus mitis* 02mitCB1 | 0.6 |
| *Streptococcus pneumoniae* 032UC1 | 0.3 |
| *Streptococcus pneumoniae* 030GR20 | 0.15 |

Conclusion: the product of Example 2 had an useful antibiotic activity.

Various modifications of the products and method of the invention may be made without departing from the spirit or scope thereof and it is to be understood that the invention is intended to be limited only as defined in the appended claims.

What is claimed is:

1. A compound of the formula

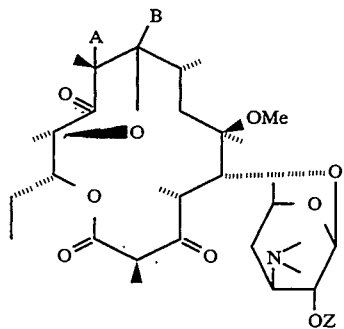

wherein A and B are both hydrogen or A is hydrogen and B is —OH or A and B form a carbon-carbon double bone and Z is hydrogen or acyl of an organic carboxylic acid of 1 to 6 carbon atoms and their non-toxic, pharmaceutically acceptable acid addition salts.

2. A compound of claim 1 wherein Z is hydrogen.

3. A compound of claim 1 wherein A and B form a carbon-carbon double bond.

4. A compound of claim 1 which is 3-de((2,6-dideoxy-3-C-methyl-3-O-methyl-α-L-ribohexopyranosyl)-oxy)-9-deoxo-9,10-didehydro-11,12-dideoxy-3,11-dioxo-9,12-epoxy-6-O-methyl-erythromycin.

5. An antibacterial composition comprising an antibacterially effective amount of a compound of claim 1 and an inert pharmaceutical carrier.

6. A composition of claim 5 wherein in the compound Z is hydrogen.

7. A composition of claim 5 wherein in the compound A and B form a carbon-carbon double bond.

8. A composition of claim 5 wherein the compound is 3-de((2,6-dideoxy-3-C-methyl-3-O-methyl-α-L-ribohexopyranosyl)-oxy)-9-deoxo-9,10-didehydro-11,12-dideoxy-3,11-dioxo-9,12-epoxy-6-O-methyl-erythromycin.

9. A method of treating bacterial infections in warm-blooded animals comprising administering to warm-blooded animals an antibacterially effective amount of a compound of claim 1.

10. The method of claim 9 wherein in the compound Z is hydrogen.

11. The method of claim 9 wherein in the compound A and B form a carbon-carbon double bond.

12. The method of claim 9 wherein the compound is 3-de((2,6-dideoxy-3-C-methyl-3 -O-methyl-α-L-ribohexopyranosyl)-oxy)-9-deoxo-9,10-didehydro-11,12-dideoxy-3,11-dioxo-9,12-epoxy-6-O-methyl-erythromycin.

* * * * *